United States Patent
Gupta et al.

(10) Patent No.: US 12,087,407 B2
(45) Date of Patent: Sep. 10, 2024

(54) USING MACHINE LEARNING FOR GENERATING CHEMICAL PRODUCT FORMULATIONS

(71) Applicant: ACCENTURE GLOBAL SOLUTIONS LIMITED, Dublin (IE)

(72) Inventors: Vivek Gupta, Gurgaon (IN); Shreeballav Sahoo, Bangalore (IN); Amar Ratanlal Bafna, Palghar (IN)

(73) Assignee: ACCENTURE GLOBAL SOLUTIONS LIMITED, Dublin (IE)

( * ) Notice: Subject to any disclaimer, the term of this patent is extended or adjusted under 35 U.S.C. 154(b) by 820 days.

(21) Appl. No.: 16/811,844

(22) Filed: Mar. 6, 2020

(65) Prior Publication Data
US 2021/0280276 A1   Sep. 9, 2021

(51) Int. Cl.
*G16C 20/10* (2019.01)
*G06F 3/0482* (2013.01)
(Continued)

(52) U.S. Cl.
CPC ........... *G16C 20/10* (2019.02); *G06F 3/0482* (2013.01); *G06F 18/2113* (2023.01); *G06N 3/08* (2013.01);
(Continued)

(58) Field of Classification Search
CPC ........ G16C 20/10; G16C 20/70; G16C 20/50; G16C 60/00; G16C 20/30; G16C 20/64; G16C 20/20; G16C 20/80; G16C 20/60; G16C 20/62; G16C 20/90; G16C 10/00; G16C 20/40; G16B 5/00; G06K 9/623
See application file for complete search history.

(56) References Cited

U.S. PATENT DOCUMENTS

| | | | |
|---|---|---|---|
| 2004/0210396 A1* | 10/2004 | Fischer | G16C 20/90 702/22 |
| 2021/0065851 A1* | 3/2021 | Madrid | G16C 10/00 |
| 2022/0101453 A1* | 3/2022 | Steppan | G16C 60/00 |

FOREIGN PATENT DOCUMENTS

| | | |
|---|---|---|
| CN | 109872780 | 6/2019 |
| WO | 2020/007962 | 1/2020 |

OTHER PUBLICATIONS

S. Sivagama Sundhari, "A knowledge discovery using decision tree by Gini coefficient," 2011 International Conference on Business, Engineering and Industrial Applications, 2011, pp. 232-235, doi: 10.1109/ICBEIA.2011.5994250. (Year: 2011).*

(Continued)

*Primary Examiner* — Lori A. Clow
*Assistant Examiner* — Emilie A Neulen
(74) *Attorney, Agent, or Firm* — Mannava & Kang, P.C.

(57) ABSTRACT

A chemical product formulation system automatically generates seed formulae from historic experiments data for the synthesis of a chemical product. Independent and dependent features are identified from the historic experiments data and feature importance scores are calculated using a supervised machine learning (ML) model. The feature importance scores are used to build data structures from which analytical rules are extracted. The analytical rules are further processed to derive the seed formulae which are user-editable. The intermediate formulae generated via user edits of the seed formulae are further validated and approved in order to be used as the final formulae which are employed for the synthesis of the chemical product.

17 Claims, 12 Drawing Sheets

(51) Int. Cl.
  *G06F 18/2113* (2023.01)
  *G06N 3/08* (2023.01)
  *G06N 5/01* (2023.01)
  *G06N 20/00* (2019.01)
  *G16C 20/70* (2019.01)
  *G16C 20/80* (2019.01)

(52) U.S. Cl.
  CPC .............. *G06N 5/01* (2023.01); *G06N 20/00* (2019.01); *G16C 20/70* (2019.02); *G16C 20/80* (2019.02)

(56) References Cited

OTHER PUBLICATIONS

André Altmann, Laura Toloşi, Oliver Sander, Thomas Lengauer, Permutation importance: a corrected feature importance measure, Bioinformatics, vol. 26, Issue 10, May 15, 2010, pp. 1340-1347, https://doi.org/10.1093/bioinformatics/btq134 (Year: 2010).*

"How to export data from Context Menu to a text file", Sep. 2017, Telerik Forums, https://www.telerik.com/forums/how-to-export-data-from-context-menu-to-a-text-file (Year: 2017).*

Raccuglia, P., Elbert, K., Adler, P. et al. Machine-learning-assisted materials discovery using failed experiments. Nature 533, 73-76 (2016). https://doi.org/10.1038/nature17439 (Year: 2016).*

Feng et al., "Computational Chemical Synthesis Analysis and Pathway Design", Frontiers in Chemistry, vol. 6, No. 199, Jun. 5, 2018, pp. 1-10.

De Almeida et al., "Synthetic organic chemistry driven by artificial intelligence", Nature Reviews Chemistry, Nature Publishing Group UK, London, vol. 3, No. 10, Aug. 21, 2019, pp. 589-604.

Coley et al., "A robotic platform for flow synthesis of organic compounds informed by AI planning", Science, vol. 365, No. 6453, Aug. 9, 2019, 10 pages.

Segler et al., "Planning chemical syntheses with deep neural networks and symbolic AI", Nature, vol. 555, No. 7698, Mar. 29, 2018, pp. 604-610.

Butler et al., "Machine learning for molecular and materials science", Nature, MacMillan Journals Ltd., Etc, London, vol. 559, No. 7715, Jul. 26, 2018, pp. 547-555.

Hippe, "Logic of human-system-interaction in planning complex strategies for chemical syntheses", 2013 6th International Conference on Human System Interactions (HSI), IEEE, Jun. 6, 2013, pp. 368-371.

Yang et al., "Deep learning for in vitro prediction of pharmaceutical formulations", ACTA Pharmaceutica Sinica B, vol. 9, No. 1, Sep. 28, 2018, pp. 177-185.

* cited by examiner

| fixed acidity | volatile acidity | citric acid | residual sugar | chlorides | free sulfur dioxide | total sulfur dioxide | density | pH | sulphates | alcohol | quality |
|---|---|---|---|---|---|---|---|---|---|---|---|
| 7.40 | 0.70 | 0.00 | 1.90 | 0.08 | 11.00 | 34.00 | 1.00 | 3.51 | 0.56 | 9.40 | 5 |
| 7.80 | 0.88 | 0.00 | 2.60 | 0.10 | 25.00 | 67.00 | 1.00 | 3.20 | 0.68 | 9.80 | 5 |
| 7.80 | 0.76 | 0.04 | 2.30 | 0.09 | 15.00 | 54.00 | 1.00 | 3.26 | 0.65 | 9.80 | 5 |
| 11.20 | 0.28 | 0.56 | 1.90 | 0.08 | 17.00 | 60.00 | 1.00 | 3.16 | 0.58 | 9.80 | 6 |
| 7.40 | 0.70 | 0.00 | 1.90 | 0.08 | 11.00 | 34.00 | 1.00 | 3.51 | 0.56 | 9.40 | 5 |
| 7.40 | 0.66 | 0.00 | 1.80 | 0.08 | 13.00 | 40.00 | 1.00 | 3.51 | 0.56 | 9.40 | 5 |
| 7.90 | 0.60 | 0.06 | 1.60 | 0.07 | 15.00 | 59.00 | 1.00 | 3.30 | 0.46 | 9.40 | 5 |
| 7.30 | 0.65 | 0.00 | 1.20 | 0.07 | 15.00 | 21.00 | 0.99 | 3.39 | 0.47 | 10.00 | 7 |
| 7.80 | 0.58 | 0.02 | 2.00 | 0.07 | 9.00 | 18.00 | 1.00 | 3.36 | 0.57 | 9.50 | 7 |
| 7.50 | 0.50 | 0.36 | 6.10 | 0.07 | 17.00 | 102.00 | 1.00 | 3.35 | 0.80 | 10.50 | 5 |
| 6.70 | 0.58 | 0.08 | 1.80 | 0.10 | 15.00 | 65.00 | 1.00 | 3.28 | 0.54 | 9.20 | 5 |
| 7.50 | 0.50 | 0.36 | 6.10 | 0.07 | 17.00 | 102.00 | 1.00 | 3.35 | 0.80 | 10.50 | 5 |
| 5.60 | 0.62 | 0.00 | 1.60 | 0.09 | 16.00 | 59.00 | 0.99 | 3.58 | 0.52 | 9.90 | 5 |
| 7.80 | 0.61 | 0.29 | 1.60 | 0.11 | 9.00 | 29.00 | 1.00 | 3.26 | 1.56 | 9.10 | 5 |
| 8.90 | 0.62 | 0.18 | 3.80 | 0.18 | 52.00 | 145.00 | 1.00 | 3.16 | 0.88 | 9.20 | 5 |
| 8.90 | 0.62 | 0.19 | 3.90 | 0.17 | 51.00 | 148.00 | 1.00 | 3.17 | 0.93 | 9.20 | 5 |
| 8.50 | 0.28 | 0.56 | 1.80 | 0.09 | 35.00 | 103.00 | 1.00 | 3.30 | 0.75 | 10.50 | 7 |
| 8.10 | 0.56 | 0.28 | 1.70 | 0.37 | 16.00 | 56.00 | 1.00 | 3.11 | 1.28 | 9.30 | 5 |
| 7.40 | 0.59 | 0.08 | 4.40 | 0.09 | 6.00 | 29.00 | 1.00 | 3.38 | 0.50 | 9.00 | 4 |
| 7.90 | 0.32 | 0.51 | 1.80 | 0.34 | 17.00 | 56.00 | 1.00 | 3.04 | 1.08 | 9.20 | 6 |
| 8.90 | 0.22 | 0.48 | 1.80 | 0.08 | 29.00 | 60.00 | 1.00 | 3.39 | 0.53 | 9.40 | 6 |
| 7.60 | 0.39 | 0.31 | 2.30 | 0.08 | 23.00 | 71.00 | 1.00 | 3.52 | 0.65 | 9.70 | 5 |
| 7.90 | 0.43 | 0.21 | 1.60 | 0.11 | 10.00 | 37.00 | 1.00 | 3.17 | 0.91 | 9.50 | 5 |
| 8.50 | 0.49 | 0.11 | 2.30 | 0.08 | 9.00 | 67.00 | 1.00 | 3.17 | 0.53 | 9.40 | 5 |
| 6.90 | 0.40 | 0.14 | 2.40 | 0.09 | 21.00 | 40.00 | 1.00 | 3.43 | 0.63 | 9.70 | 6 |
| 6.30 | 0.39 | 0.16 | 1.40 | 0.08 | 11.00 | 23.00 | 1.00 | 3.34 | 0.56 | 9.30 | 5 |
| 7.60 | 0.41 | 0.24 | 1.80 | 0.08 | 4.00 | 11.00 | 1.00 | 3.28 | 0.59 | 9.50 | 5 |

FIG. 7

| RULE_NO | PRODUCT | TARGET_STATE | INGREDIENTS | UNIT | MIN OPERATOR | MIN | MAX OPERATOR | MAX |
|---|---|---|---|---|---|---|---|---|
| 1 | RED WINE | 5 | ALCOHOL | % | | 8.50 | <= | 10.25 |
| 1 | RED WINE | 5 | SULPHATES | g/ltr | | 0.37 | <= | 0.58 |
| 1 | RED WINE | 5 | TOTAL SULFUR DIOXIDE | mg/ltr | | 6.00 | <= | 98.50 |
| 2 | RED WINE | 5 | ALCOHOL | % | | 8.50 | <= | 10.25 |
| 2 | RED WINE | 5 | SULPHATES | g/ltr | | 0.37 | <= | 0.58 |
| 2 | RED WINE | 5 | TOTAL SULFUR DIOXIDE | mg/ltr | > | 98.50 | | 155.00 |
| 3 | RED WINE | 5 | ALCOHOL | % | | 8.50 | <= | 10.25 |
| 3 | RED WINE | 5 | SULPHATES | g/ltr | > | 0.58 | <= | 1.98 |
| 3 | RED WINE | 5 | TOTAL SULFUR DIOXIDE | mg/ltr | | 6.00 | <= | 81.50 |
| 4 | RED WINE | 5 | ALCOHOL | % | | 8.50 | <= | 10.25 |
| 4 | RED WINE | 5 | SULPHATES | g/ltr | > | 0.58 | <= | 1.98 |
| 4 | RED WINE | 5 | TOTAL SULFUR DIOXIDE | mg/ltr | > | 81.50 | | 155.00 |
| 5 | RED WINE | 6 | ALCOHOL | % | > | 10.25 | <= | 11.55 |
| 5 | RED WINE | 6 | VOLATILE ACIDITY | g/ltr | > | 0.16 | <= | 0.38 |
| 6 | RED WINE | 6 | ALCOHOL | % | > | 10.25 | <= | 11.55 |
| 6 | RED WINE | 6 | VOLATILE ACIDITY | g/ltr | > | 0.38 | <= | 1.04 |
| 7 | RED WINE | 6 | ALCOHOL | % | > | 11.55 | | 14.00 |
| 7 | RED WINE | 6 | SULPHATES | g/ltr | | 0.40 | | 0.69 |

FIG. 10

*1100* accenture

DIGITAL CHEMIST

Q WELCOME, LINDA
SCIENTIST

< HOME

RECOMMENDED FORMULATIONS

QUALITY 5 — 1102 ▸ COUNTRY UK (+1 OTHERS) — 1104 ▸ ITEMS PER PAGE 10 — 1106 ▸ SHOWING 1 - 10 OUT OF 11 ENTRIES — 1108 ⌄

∞ DEMO_26JUN_V1

| ALCOHOL | + | SULPHATES | + | TOTAL SULFUR DIOXIDE  1110 |
| 10 % | | 0.575 g/ltr | | 81.5 mg/ltr |

∞ DEMO_14JUN_V1

| ALCOHOL | + | SULPHATES | + | TOTAL SULFUR DIOXIDE  1120 |
| 10 % | | 0.575 g/ltr | | 98.5 mg/ltr |

∞ TEST1

| ALCOHOL | + | SULPHATES | + | TOTAL SULFUR DIOXIDE  1130 |
| 12 % | | 0.575 g/ltr | | 81.5 mg/ltr |

∞ DEMO_14JUN_V6

| ALCOHOL | + | SULPHATES | + | TOTAL SULFUR DIOXIDE |
| 10 % | | 0.575 g/ltr | | 98.5 mg/ltr |

COPYRIGHT 2019 ACCENTURE. ALL RIGHTS RESERVED.

*FIG. 11*

USING MACHINE LEARNING FOR GENERATING CHEMICAL PRODUCT FORMULATIONS

BACKGROUND

Artificial Intelligence is having a significant impact on many industries to optimize day-to-day operations, create an enhanced customer experience, and most importantly in Research and Development (R & D) of new products. R & D helps to strengthen an organization's top line and bottom lines. In the chemical and pharmaceutical industry, R & D plays a vital role as it is a key driver for future sustainability and to create a competitive advantage. Such organizations continuously face demands to shorten the product development lifecycle while facing delays in product launches due to trial and error methods during the research and development new products. Moreover, stringent compliance policies laid down by regulators and shortages of skilled manpower coupled with aging workforce in R&D divisions of Chemical, Petro-Chemical and Pharmaceutical industry have become hurdles for generating new product formulations in the laboratories.

BRIEF DESCRIPTION OF DRAWINGS

Features of the present disclosure are illustrated by way of examples shown in the following figures. In the following figures, like numerals indicate like elements, in which:

FIG. 7 shows a table that includes a sample historic experiments data set related to making wine.

FIG. 10 shows a table of analytical rules generated in accordance with the examples disclosed herein.

FIG. 11 shows a formulation graphical user interface (GUI) that enables users to generate intermediate formulae from seed formulae in accordance with the examples disclosed herein.

DETAILED DESCRIPTION

Figure 1:
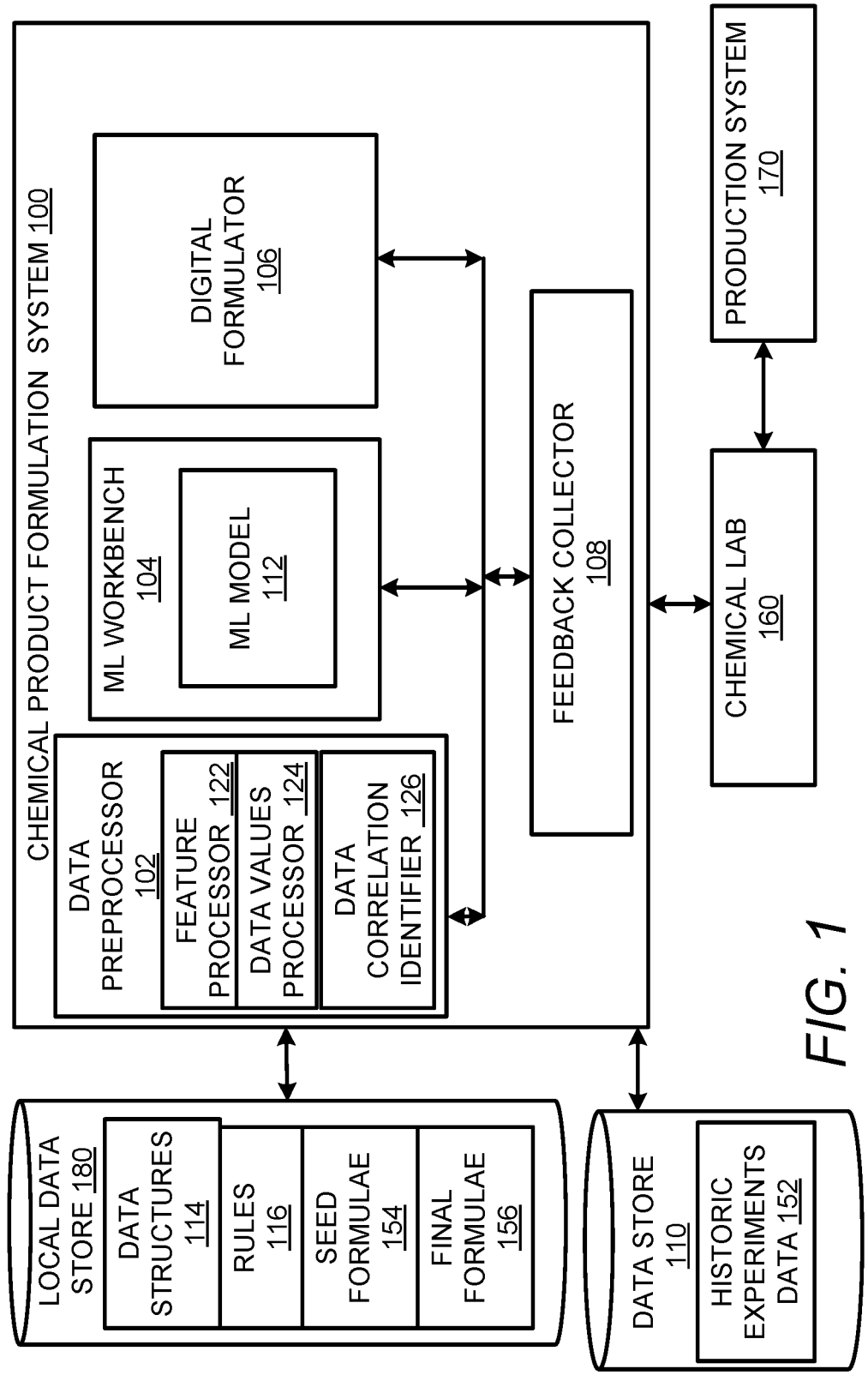
FIG. 1 shows a block diagram of a chemical product formulation system in accordance with the examples disclosed herein.

For simplicity and illustrative purposes, the present disclosure is described by referring to examples thereof. In the following description, numerous specific details are set forth in order to provide a thorough understanding of the present disclosure. It will be readily apparent however that the present disclosure may be practiced without limitation to these specific details. In other instances, some methods and structures have not been described in detail so as not to unnecessarily obscure the present disclosure. Throughout the present disclosure, the terms "a" and "an" are intended to denote at least one of a particular element. As used herein, the term "includes" means includes but not limited to, the term "including" means including but not limited to. The term "based on" means based at least in part on.

A chemical product formulation system that automatically generates seed formulae from historic experiments data for the synthesis of the chemical product is disclosed. The historic experiments data includes ingredients and the amounts of ingredients used in prior experiments that were conducted to develop a formulation for the chemical product. In an example, the historic experiments data may also include certain product or process attributes and the results or outcomes of the experiments. The historic experiments data is initially preprocessed to address data sufficiency issues and for processing outliers. The independent and dependent features are identified from the preprocessed data wherein the independent features include those features such as the ingredients that were used and the amounts of ingredients used which can be varied by a scientist or other user conducting the experiments. Dependent features include features that are expected or targeted as results of the experiments and hence these features are dependent on the independent features. For example, the quality of the chemical product which is expected as a result of an experiment can be a dependent feature. In addition, the inter and intra relationships between the features are also established during the data preprocessing stage.

The preprocessed data is fed to a supervised ML model for calculation of feature importance scores. In an example, the supervised ML model can include random forests. The feature importance score for a given feature, when obtained from the random forest model, is calculated as the average feature importance scores of the feature from all the decision trees within the random forest model. The feature importance scores are then normalized. The feature importance scores are used to construct data structures such as the CARTS. When the CART is used, Gini index is used as a metric or cost function to evaluate split in feature selection in case of a classification tree and least square is used as a metric to select features in case of a Regression tree. When Gini index is used, the feature with the lowest Gini index can be chosen as the root node for the data structure.

The data structures thus generated are used for extracting analytical rules. The analytical rules include conditions related to the ingredients to be added for making the chemical product, the limits or ranges on the quantities of ingredients to be added and specifications regarding the final chemical product to be manufactured. The analytic rules are generated by extracting the attributes of the various nodes in the data structures. The extracted node attributes can include feature names, numerical values, mathematical operators and a target state. The analytic rules can be stored in one or more formats.

The analytical rules are used to automatically generate seed formulae for the synthesis of the chemical product. Each seed formula includes one or more ingredients and the amounts of the ingredients that can be added. In an example, a seed formula can include the amount of an ingredient as a range with the minimum and the maximum quantities that can be added. The seed formulae that are automatically generated are further subject to verification in order to determine compliance with regulations of a particular jurisdiction. The verification process can be configured to disallow the generation of seed formulae that fail to comply with the regulation of a selected jurisdiction. Different jurisdictions can be selected for the application of different regulatory requirements against the seed formulae. The seed formulae are provided to a user via a formulation GUI which allows the user to select or change preselected quantity values in the seed formulae in accordance with the regulatory restrictions from the selected jurisdiction. Intermediate formulae thus generated by the user are provided to a supervisory user for validation. The validated intermediate formulae are stored as the final formulae for the synthesis of the chemical product. The final formulae can be provided to a chemical lab for further testing and the tested final formulae are provided to a production plant for the large-scale manufacturing of the chemical product. The post-production data from the production plant can be fed back to the historic experiments data so that the success and failures of the automatically-generated seed formulae are monitored and recorded. In an example, a conversational virtual agent that uses natural language processing (NLP) to communicate with humans via text or voice eases the interaction between the chemical product formulation system and its human users.

The chemical product formulation system as disclosed herein enables a framework of cognitive and data services to accelerate innovation in the R & D of chemical industries. The chemical product formulation system functions as an Artificial Intelligence (AI) powered digital twin, augmenting and learning from human chemists across the chemical product life cycle from R & D to production. With usage over time, the chemical product formulation system can enable the creation of new products and formulations thereby making it possible to leverage "swarm intelligence" across an organization. The chemical product formulation system thus enables users to discover formulae for a chemical product that were previously undetected by human users. Furthermore, the calculation of dependent features enables the prediction of attribute values and properties without actually carrying out the physical experiments. The formulation GUI enables users to dynamically adjust the chemical formulae thereby providing the users with an opportunity to study "What-if" scenarios prior to carrying out the actual experiments in the laboratory. Thus, the chemical product formulation system disclosed herein improves chemical production processes via improving the efficiency of the production process and the quality of the chemical product produced from such processes.

FIG. 1 shows a block diagram of a chemical product formulation system 100 that automatically generates seed formulae for the synthesis of chemical products and feeds the final formulae to a production system thereby enabling an efficient production system for chemical products in accordance with the examples disclosed herein. The chemical product formulation system 100 includes a data preprocessor 102, an ML workbench 104, a digital formulator 106 and a feedback collector 108. The chemical product formulation system 100 includes or may be communicatively coupled to a data store 110 with historic experiments data 152 that includes data regarding the various experiments that were carried out in a lab for producing a chemical product. The historic experiments data 152 can include the various ingredients and the quantities of the ingredients that were used, and process attributes that were applied during the experiments as well as outcomes of the experiments. The historic experiments data is accessed by the chemical product formulation system 100 for analysis and production of the seed formulae 154. The data preprocessor 102 processes the historic experiments data 152 that enables an ML model 112 to produce feature importance scores which are employed for selecting features to be used in building the seed formulae 154. The digital formulator 106 presents the seed formulae 154 for validation and obtains one or more final formulae 156 which are provided to a chemical lab 160 for investigation. The results of the experimental investigation from the chemical lab 160 can be received by the chemical product formulation system 100 for further validation prior to the final formulae 156 being passed on to a production system 170 for large scale synthesis of the chemical product. Based on the chemical domain associated with the historic experiments data, a specific ML model can be developed by the chemical product formulation system 100. Therefore, the chemical product formulation system 100 can be configured to generate the seed formulae for the synthesis of a variety of chemical products including but not limited to, food products, pharmaceuticals, cosmetics, industrial chemicals, etc. In an example, the chemical product formulation system 100 can include a local data store 180 for storing seed formulae 154, the final formulae 156, etc.

The data preprocessor 102 includes a feature processor 122, a data values processor 124 and a data correlation identifier 126. The historic experiments data 152 can be in a structured data format, a flat-file format or stored in a relational database management system (RDBMS). The feature processor 122 is configured to identify if the data is in a format that can be processed by the remaining components, e.g., the ML workbench 104, etc. The feature processor 122 can also be configured to identify the nature or data format of the different fields within the historic experiments data 152 such as whether a field includes textual data, numeric data, etc. The data values processor 124 determines missing data values, outliers, etc. For missing numeric data values, the data value processor 124 may automatically fill the values with the average value of the corresponding field. The data correlation identifier 126 receives information regarding the target (dependent) and the explanatory (independent) variables. Furthermore, the inter-relationships between the target and the explanatory variables and the intra-relationships between the explanatory variables may also be derived. In an example, a user may identify the target and explanatory variables and further supply the information regarding the inter-relationships and the intra-relationships between them. The correlations between the different variables can aid in designing seed formulae since not only are the desirable attributes identified, but also the features affecting the desirable attributes may be gathered by the data correlation identifier 126 via the correlations.

The historic experiments data 152 processed by the data preprocessor 102 and the informational analysis including the variable correlations gathered from the historic experiments data 152 are provided to the ML workbench 104 which identifies the independent and dependent variables for modeling from the preprocessed historic experiments data. A supervised ML algorithm is used to obtain feature importance scores based on which features are selected to build a data structure. As mentioned above, different chemical products may have different profiles as conveyed by the historic experiments data. Accordingly, different supervised ML algorithms such as but not limited to, decision trees, random forests, can be used for generating seed formulae for the synthesis of different chemical products. The ML model 112 to be used can be identified based on different validation metrics. In an example, the chemical product formulation system 100 can thus be configured to process historic experiments data related to a single chemical product and generate the seed formulae for that chemical product based on a given ML model. Similarly, another formulation system can be configured to analyze historic experiments data related to another chemical product and generate seed formulae for the other chemical product based on a different ML model. The feature importance scores are used to build one or more data structures 114 that encode process information for the synthesis of the chemical product as conveyed in the historic experiments data 152. In an example, the data structures 114 can include decision trees wherein the nodes of the trees are determined based on the feature importance scores. The data structures 114 are further processed to extract analytical rules 116. The analytical rules 116 include the ingredients and quantity thresholds associated with the ingredients for the synthesis of the chemical product and may be stored in different formats including textual data files. The analytical rules 116 are used to generate the seed formulae 154. In an example, the analytical rules 116 can include ingredient proportions based not only on the analytical rules 116 but also in compliance with any regulatory requirements for jurisdictions for which the seed formulae 154 are generated.

The seed formulae 154 are provided to the digital formulator 106. The digital formulator 106 enables validation of the seed formula 154 by presenting the seed formulae 154 to a user on a formula simulation graphical user interface (GUI). As mentioned above, the seed formulae 154 include quantity threshold values that can be used for the chemical product synthesis. The formula simulation GUI enables a user to provide or select specific values for the quantities of ingredients to be used in the synthesis from the permissible ranges displayed on the formula simulation GUI. When the user determines that the appropriate ingredients and the requisite quantities for the ingredients, the user can save the formula as an intermediate formula. Multiple such intermediate formulae can thus be generated and stored by the user. The intermediate formulae when approved by the supervisory user are stored as the final formulae 156.

The final formulae 156 thus produced can be provided to the chemical lab for investigations. If one or more of the final formulae 156 are found valid, the validated final formulae can be provided to the production system 170. The data from one or more of the chemical labs 160 and the production system 170 is collected by the feedback collector 108. The feedback collector 108 can add the result or outcomes of the final formulae that were successfully implemented as well as the failed final formulae to the historic experiments data 152.

Figure 2:
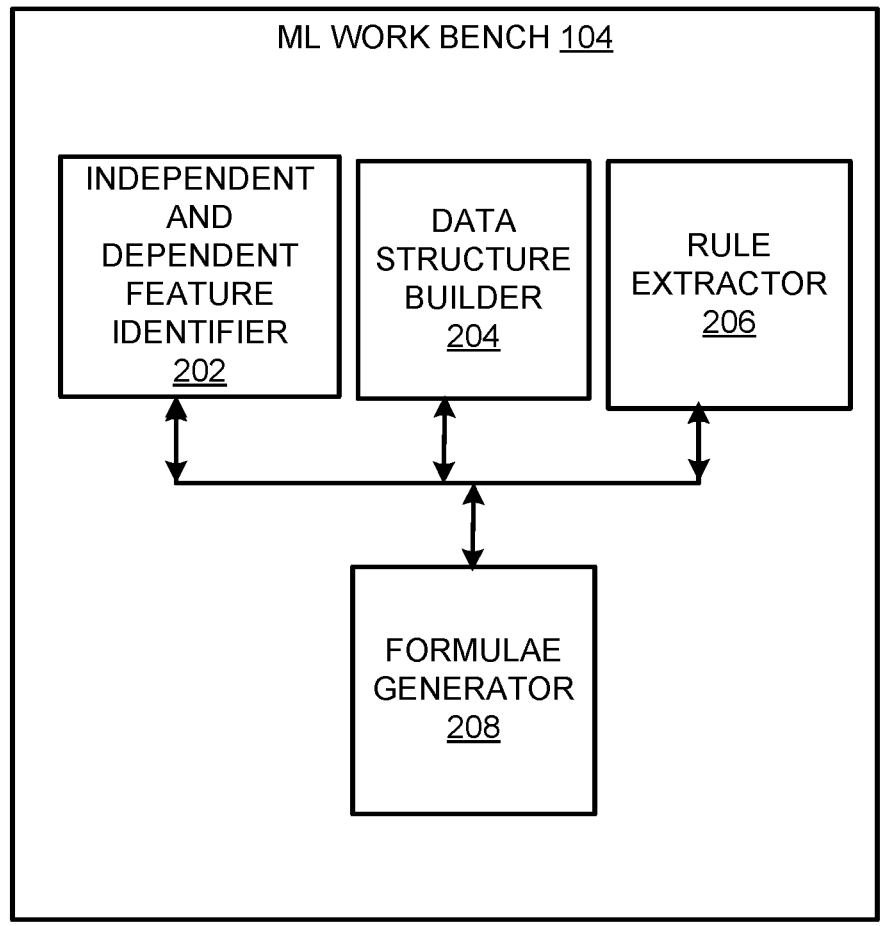
FIG. 2 shows a block diagram of a machine learning (ML) workbench in accordance with the examples disclosed herein.

FIG. 2 shows a block diagram of the ML workbench 104 in accordance with the examples disclosed herein. The ML workbench 104 includes an independent and dependent feature identifier 202, a data structure builder 204, a rule extractor 206 and a formulae generator 208. In an example, the ML workbench 104 can include the ML model 112 which is based on a supervised ML algorithm and trained to produce feature importance scores that are used to construct the data structures 114 and hence aid in rule extraction. In the following description, reference may be made to certain types of historic experiments data for illustration purposes. It may be appreciated that the chemical product formulation system 100 is not limited to the particular data discussed herein but may also be used to process historic experiments data of other types of chemical products and to produce seed formulae for such chemical products.

The independent and dependent feature identifier 202 accesses processed data produced by the data preprocessor 102 from the historic experiments data 152 to additionally identify independent and dependent features. In an example, a user may identify the independent and dependent features in the historic experiments data 152. Referring to an experiments data set including data regarding wine formulations, independent features may include attributes of the wine such as fixed acidity, volatile acidity, pH, density, etc. Additionally, quantities of free sulfur dioxide, total sulfur dioxide, alcohol, sulfates, etc. can also be considered as independent features. Dependent features may include quality, color, taste, etc. Further examples of historic experiment data sets can include different classes for a given feature. For example, there can be three different classes for the dependent feature-quality.

The ML model 112 is employed to calculate the feature importance. In an example, the data including the independent features and the dependent features can be represented as decision trees with the ML model 112 calculating the node importance using Gini importance:

$$\text{nimp}_j = w_j C_j - w_{left(j)} C_{left(j)} - w_{right(j)} C_{right(j)} \quad \text{-Eq. (1)}$$

where, $\text{nimp}_j$=Importance of node j
$w_j$=weighted number of samples reaching node j
$C_j$=impurity value of node j
left(j)=child node from a left split on node j
right(j)=child node from a right split on node j.
The importance of each feature on a decision tree calculated as:

$$\text{fimp}_i = \frac{\sum_{j:\text{node } j \text{ splits on feature } i} \text{nimp}_j}{\sum_{k \in \text{all nodes}} \text{nimp}_k} \quad \text{Eq. (2)}$$

where, $\text{fimp}_i$=Importance of feature i
$\text{nimp}_j$=Importance of node j.
Feature importance values are normalized as:

$$\text{norm fimp}_i = \frac{\text{fimp}_i}{\sum_{j \in \text{all features}} \text{fimp}_j} \quad \text{Eq. (3)}$$

Feature importance for random forest can be calculated as:

$$\text{RF fimp}_i = \frac{\sum_{j \in \text{all trees}} \text{norm fimp}_{ij}}{T} \quad \text{Eq. (4)}$$

The final feature importance for a random forest model is averaged over all the trees.

where, $\text{RF fimp}_i$=Importance of feature i calculated from all trees in the Random Forest model, $\text{norm fimp}_{ij}$=Normalized feature importance for i in tree j and T=Total number of trees.

As different features can be associated with different classes, the problem of generating seed formulae can be treated as an ML classification problem. Different machine learning algorithms may be used for different historic experiments data sets that are generated for different chemicals. In the example data set pertaining to wine, decision trees can be employed for data representation. Multiple variants of decision trees are available including:

Classification and Regression Tree (CART)
Iterative Dichotomizer (ID 3)
Chi-square Automatic Interaction Detector (CHAID)
ID 4.5

In an example, the CART algorithm can be used for representing data pertaining to wine synthesis. The CART algorithm uses Gini index as metric/cost function to evaluate splits in feature selection in the case of a classification tree and uses the least square as a metric to select features in the case of the regression tree. Gini index is a measure of inequality in a given data sample and has values between 0 and 1. It is the sum of the square of the probabilities of each class. It is calculated as:

$$GI_{root} = 1 - \sum_{i=1}^{n} p_i^2 \quad \text{Eq. (5)}$$

where i=no. of classes. For each class, the Gini impurity value is calculated and the class which has a minimum Gini impurity value is chosen as a root node. Based on the Gini indices that are thus obtained, one or more data structures 114 can be built by the data structure builder 204. Referring to the example that includes experiments data related to wine making, it was determined that a multiclass classification ML algorithm is suitable for modeling the wine making experiments data.

There ML model 112 output can be further validated through cross table technique and multiclass ROC curve techniques. The ROC curve is the plot between sensitivity i.e. True Positive Rate and (1-specificity) i.e. False Positive Rate. The true positive rate is calculated as the number of true positives divided by the sum of the number of true positives and the number of false negatives. It describes how good the model is at predicting the positive class when the actual outcome is positive.

True Positive Rate=True Positives/(True Positives+ False Negatives)   -Eq. (6)

False Positive Rate is calculated as the number of false positives divided by the sum of the number of false positives and the number of true negatives. It is also called the false rate as it summarizes how often a positive class is predicted when the actual outcome is negative.

False Positive Rate=False Positives/(False Positives+ True Negatives)   -Eq. (7)

The data structures 114 are employed by the rule extractor 206 for extracting the analytical rules 116. In an example, the rules can be stored in tabular formats such as spreadsheets or database tables in the local data store 180. Each rule can include an ingredient and an amount of ingredient that is to be used for one or more synthesis processes for the chemical product to be produced in accordance with a target state (i.e., one of the classes to be ascribed to a target feature). In an example, the amount of an ingredient to be included for the synthesis of the chemical product can be expressed as a range when constructing the data structures 114. The range of quantity of the ingredient can be encoded into the analytical rules 116 using mathematical operators by the rule extractor 206. The analytical rules 116 including ranges for quantities of different ingredients required to synthesize the chemical product can be translated into the seed formulae 154 by the formulae generator 208. A seed formula for making wine of a given target quality includes the various ingredients to make the wine along with the ranges of quantities of the ingredients which are combined using mathematical operators that are identified based on the rules.

Figure 3:
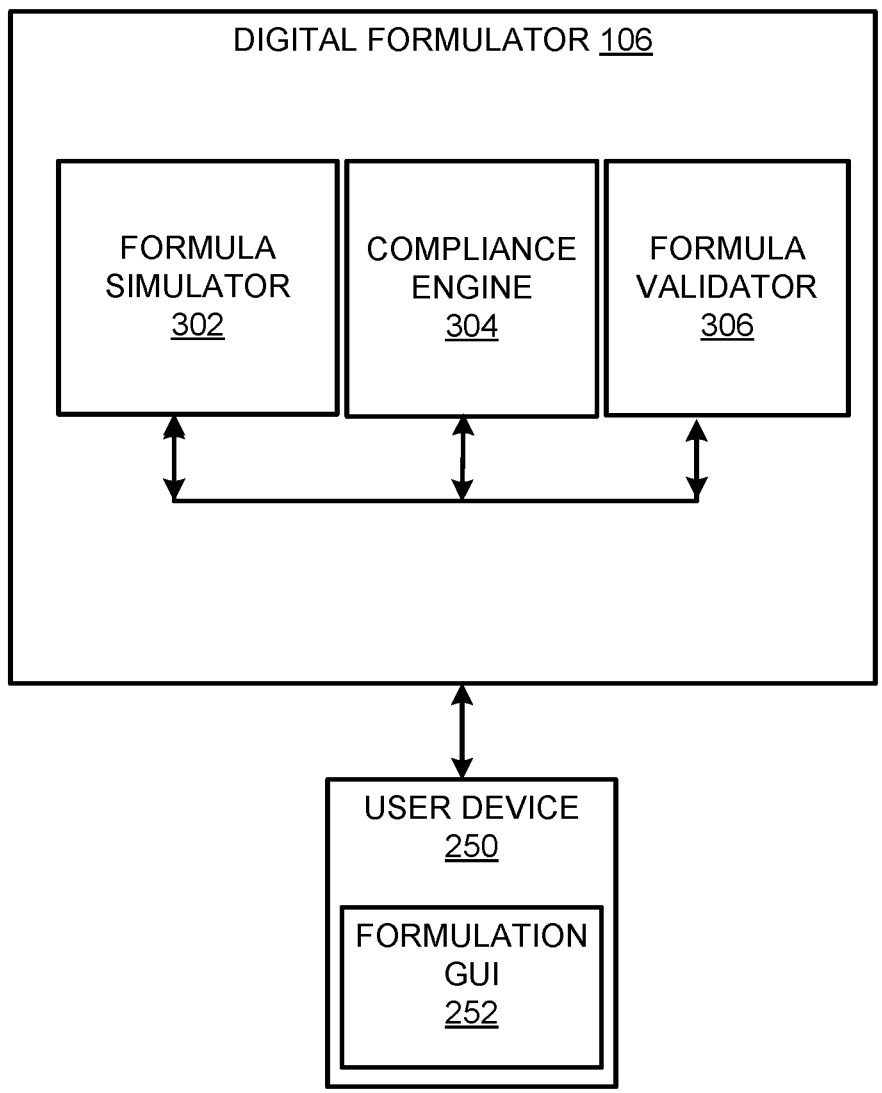
FIG. 3 shows a block diagram of a digital formulator in accordance with the examples disclosed herein.

FIG. 3 shows a block diagram of the digital formulator 106 in accordance with an example. The digital formulator 106 includes a formula simulator 302, a compliance engine 304 and a formula validator 306. The formula simulator 302 accesses the seed formulae 154 produced by the ML workbench 104 and provides the seed formulae 154 to a user for validation. In an example, the seed formulae can be presented to the user on a user device 250 via a formulation GUI 252. The formulation GUI 252 presents a seed formula including the ingredients and the quantities or quantity range thresholds in a manner that allows the user to fix quantities for one or more of the ingredients thereby generating an intermediate formula. A plurality of such intermediate formulae can be generated from each seed formula by varying the quantities of one or more of the ingredients.

The digital formulator 106 may additionally include a compliance engine 304. The compliance engine 304 can impose further restrictions on the ingredients and/or the quantity of the ingredients based on a particular jurisdiction for which the chemical product is being synthesized. Therefore, each of the plurality of intermediate formulae can be subjected to further validation by the compliance engine 304 based on a given jurisdiction. The intermediate formulae can be verified for one or more of government regulations and/or business rules. Therefore, an intermediate formula for the chemical product is subject to compliance verification at the design stage itself so that no further resources are wasted on non-compliant formulae.

The intermediate formulae thus generated are provided to a formula validator 306 which is configured to provide the intermediate formulae to another user of a specific category. For example, a supervisory user can be automatically notified of the compliant intermediate formulae via an email communication or a notification on the formulation GUI. The supervisory user can review the compliant intermediate formulae and approve or reject them. The approved intermediate formulae can be stored as the final formulae 156 which are then forwarded to the chemical lab 160 for further physical testing and implementation.

Figure 4:
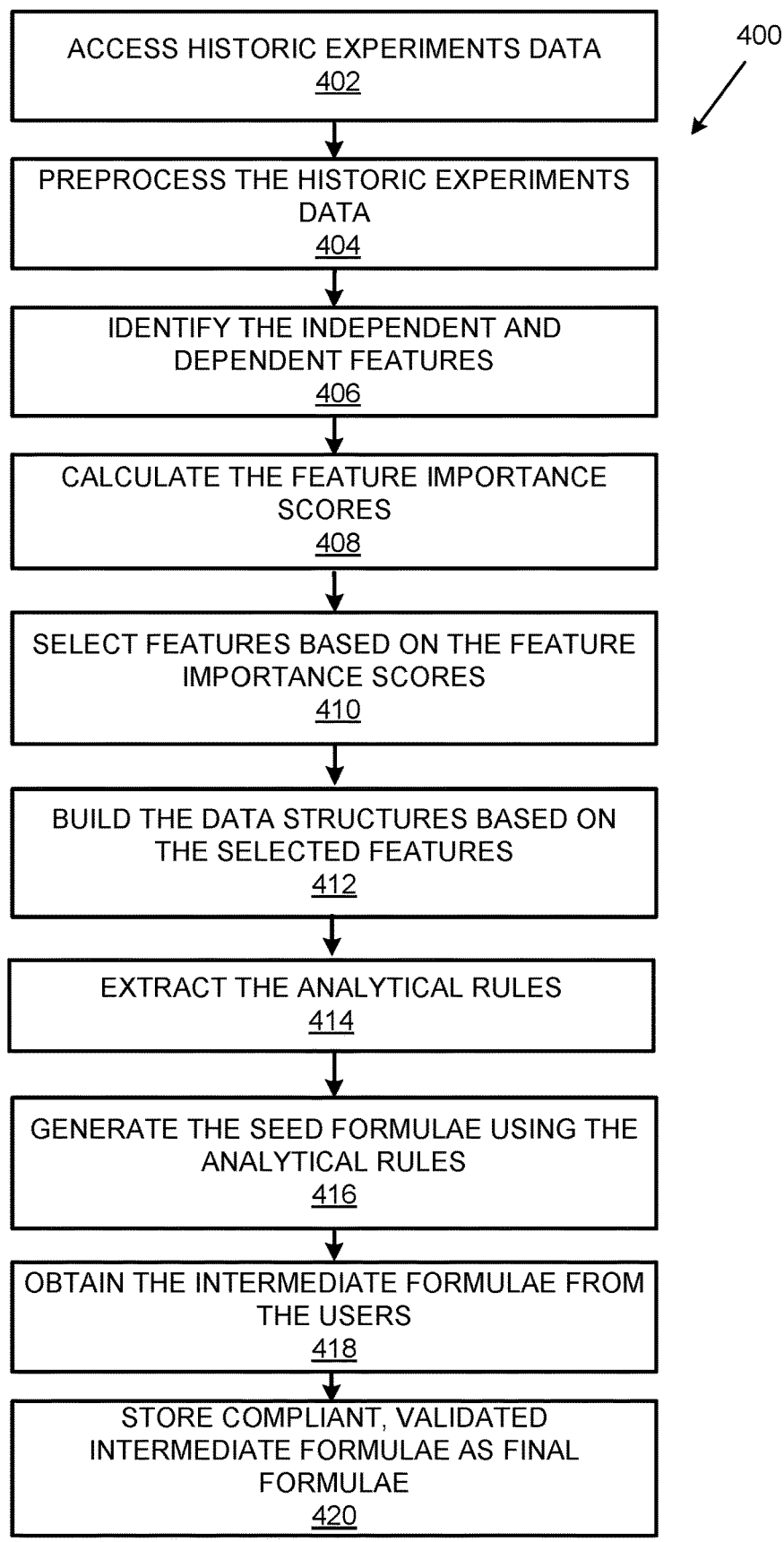
FIG. 4 shows a flowchart that details a method of automatically generating chemical formulae for the synthesis of a chemical product in accordance with an example disclosed herein.

FIG. 4 shows a flowchart 400 that details a method of automatically generating chemical formulae for the synthesis of a chemical product in accordance with an example disclosed herein. The method begins at 402 wherein the historic experiments data 152 which can include structured or unstructured data is accessed. The data may be available publicly or may be accessed only through private archives. The historic experiments data 152 can include data that is produced by conducting various experiments over a time period for generating and testing chemical formulae for producing the chemical product in the chemical lab 160 which can be eventually scaled up to the production level. The historic experiments data 152 can include not only the ingredients and the various quantities of ingredients to be used but may also include other attributes such as the quality of the chemical product that was produced, the process parameters such as the temperature, pressure, pH, acidity that was maintained, the conditions at the beginning of the production process and the conditions at the end of the production process and the outcomes of the experiments. In an example, the historic experiments data 152 can be arranged in the form of rows wherein each row corresponds to a particular experiment for producing the chemical product.

The historic experiments data 152 is preprocessed by the data preprocessor 102 at 404 for removal of outliers, data deduplication and for processing data so that there is sufficient data density by automatically filling in missing values, etc. For example, missing values for a variable may be filled up with the mean of the available values of that variable. If the historic experiments data 152 includes unstructured data then techniques such as natural language processing may be employed to convert the unstructured data to a structured format, for example, into a spreadsheet format or to populate a database table. The preprocessed data is employed to identify the independent and dependent features at 406. The independent features or explanatory features are the variables for which the values are set during the physical experimentation and the dependent features or target features may include variables whose values are determined by the independent features. At 408, feature importance scores are calculated using a supervised ML algorithm such as random forests, etc. In an example, the importance of a feature can be calculated using the trees in the random forest model. At 410, a subset of the features is selected for seed formulae generation based on the feature importance scores. In an example, the feature importance scores can indicate the impact that a particular ingredient or the quantity of the ingredient or a process parameter such as pH has on the overall synthesis of the chemical product.

The selected features are used to build the data structures 114 at 412. Different data structures can be built based on the nature of data within the historic experiments data 152. By way of illustration and not limitation, the data structures 114 built at 412 can include one of the multiple variants of decision trees such as but not limited to, CART, ID 3, CHAID, etc. When the data structures built at 412 include CART, Gini index is used as a metric/cost function to evaluate the split in the feature selection in the case of a classification tree and least squares is used as a metric to select features in the case of regression tree.

A feature having the least Gini index value is selected for the root node. At 414, the analytical rules 116 for generating the seed formulae 154 are extracted from the data structures 114. The analytical rules 116 that are extracted are used at 416 to generate the seed formulae 154. At 418, the intermediate formulae are obtained from the users. As mentioned above, the seed formulae 154 include the ingredients and the quantity ranges of the ingredients as identified from the historic experiments data 152 while the final formulae 156 include the ingredients and the quantities of the ingredients to be used for synthesizing the chemical product in a chemical lab 160. The intermediate formulae that are compliant with the rules of a given jurisdiction are provided for validation. The validated, compliant intermediate formulae are stored at 420 as the final formulae 156 and provided to the chemical lab 160 for testing.

Figure 5:
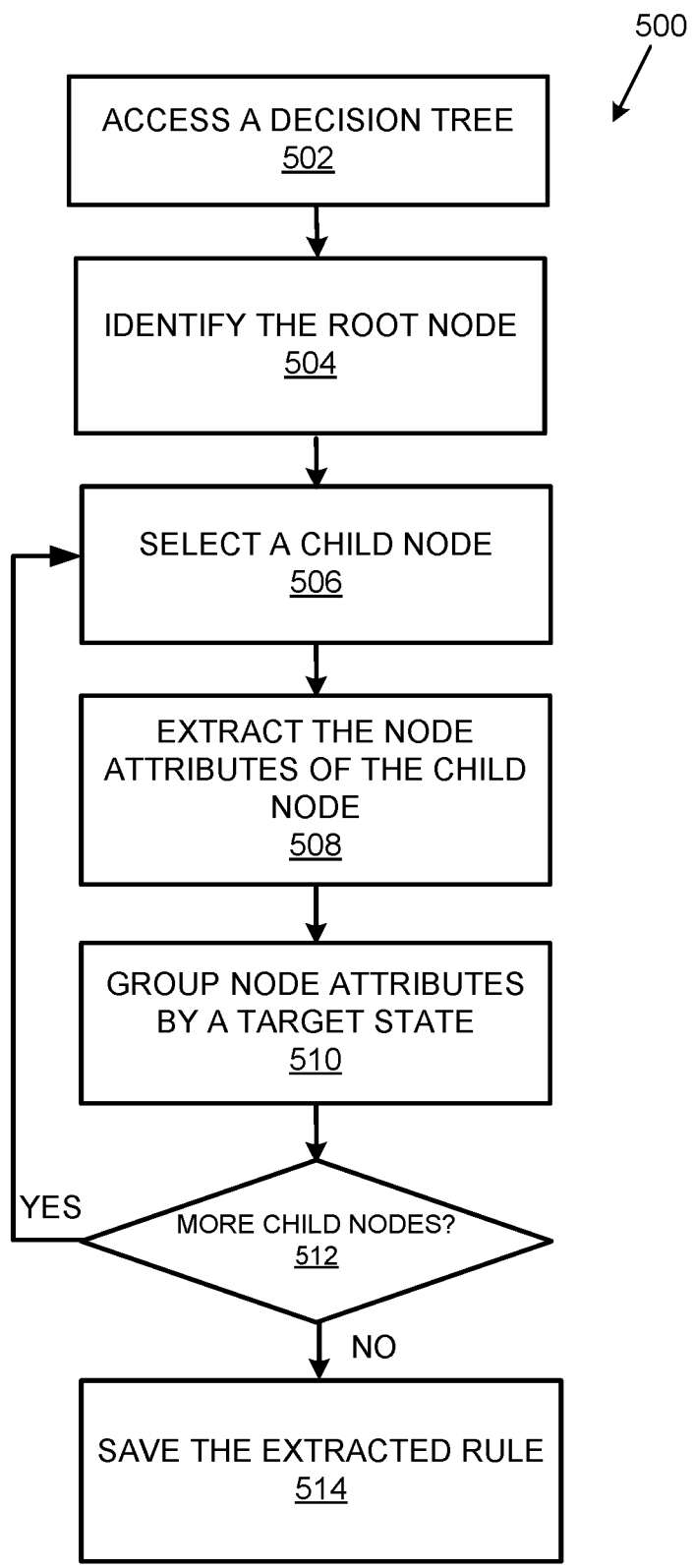
FIG. 5 shows a flowchart that details a method for extracting analytical rules in accordance with the examples disclosed herein.

FIG. 5 shows a flowchart 500 that details a method for extracting the analytical rules in accordance with the examples disclosed herein. The method begins at 502 wherein a decision tree or a CART encoding the feature information is initially accessed. The root node is identified at 504. In an example, a node with the minimum Gini index is identified as the root node. One of the child nodes of the root node is selected at 506. The node attributes of the selected node are extracted at 508. At 510, the node attributes are grouped by the target state. As mentioned above, a dependent feature can be indicative of a target state. Examples of target states can include specific process or product criteria that are to be achieved at a given point during the synthesis of the chemical product. At 512, it is determined if further child nodes remain to be processed for attribute extraction. If yes, the method returns to 506 to select the next child node, else the method proceeds to 514 wherein an extracted rule which includes the node attributes grouped by the target stat is saved to a rules database or a rules table. It can be appreciated that the extraction of the node attributes has been described here as a serial process for illustration purposes only and that the attributes of various nodes in a given CART can be extracted simultaneously in parallel processing.

Figure 6:
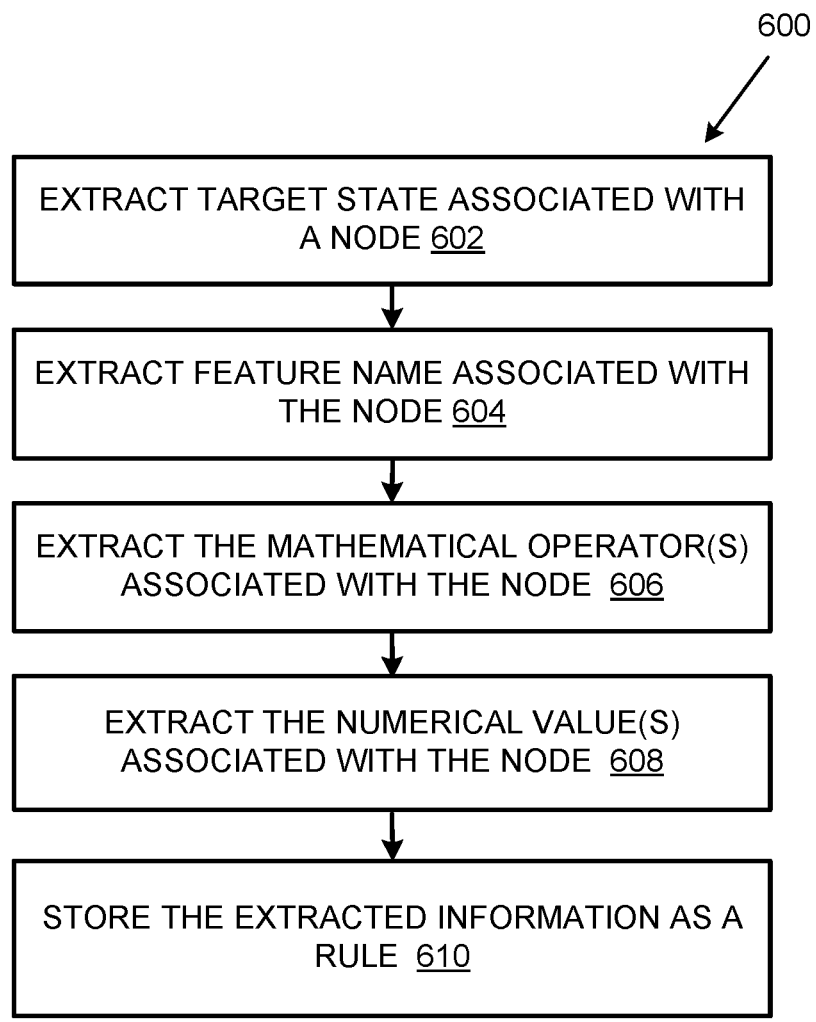
FIG. 6 shows a flowchart that details a method of extracting node attributes of a child node in the Classification and Regression Tree (CART) in accordance with the examples disclosed herein.

FIG. 6 shows a flowchart 600 that details a method of extracting the node attributes of a node in the CART in accordance with the examples disclosed herein. In an example, different techniques such as natural language processing, expression matching, regular expressions (Regex), etc. can be employed for the extraction of node attributes. As each node is processed, text-matching techniques can be employed to identify the data stored at the node. At 602, the target state associated with the node is extracted. By way of illustration and not limitation, a keyword such as 'class' can indicate the target state for the data set represented by the CART. At 604, the feature name associated with the node is extracted. Again, as the historic experiments data 152 is processed and features identified, the various keywords indicative of feature names can be stored and used with text-matching techniques to identify the feature names of the nodes in the CART. At 606, one or more mathematical operators such as but not limited to ">", "<", "=", "≤", "≥" associated with the node are extracted. At 608, one or more numerical values associated with the mathematical operators included in the node are extracted. As mentioned above, the historic experiments data 152 includes not only the ingredients but also the ingredient quantities used in the experiments. Accordingly, the quantities can be expressed as combinations of numerical values and mathematical expressions. In an example, character matching or regular expressions can be employed to identify the mathematical operators. The information associated with a child node extracted at the various steps as detailed above is stored at 610 as a rule. The analytical rules 116 can be saved as entries into files of different formats such as but not limited to comma-separated values (CSVs), JavaScript Object Notation (JSON), Extensible Markup Language (XML) formats.

FIG. 7 shows a table 700 which includes a sample historic experiments data set 750 related to making wine. Each row in table 700 represents one experiment. For each experiment, the quantity of ingredients is mentioned as well as the output of the experiment and the specifications associated with each of the experiments. The quantities of ingredients such as citric acid, chlorides, total sulfur dioxide, sulfates, alcohol, fixed acidity, density, pH, etc., are given which may be identified as independent features. Dependent features may include a target variable or a feature dependent on the aforementioned feature or 'class' includes a quality criterion. As seen from table 700, the quality feature has four different classes, 4, 5, 6 and 7.

Figure 8:
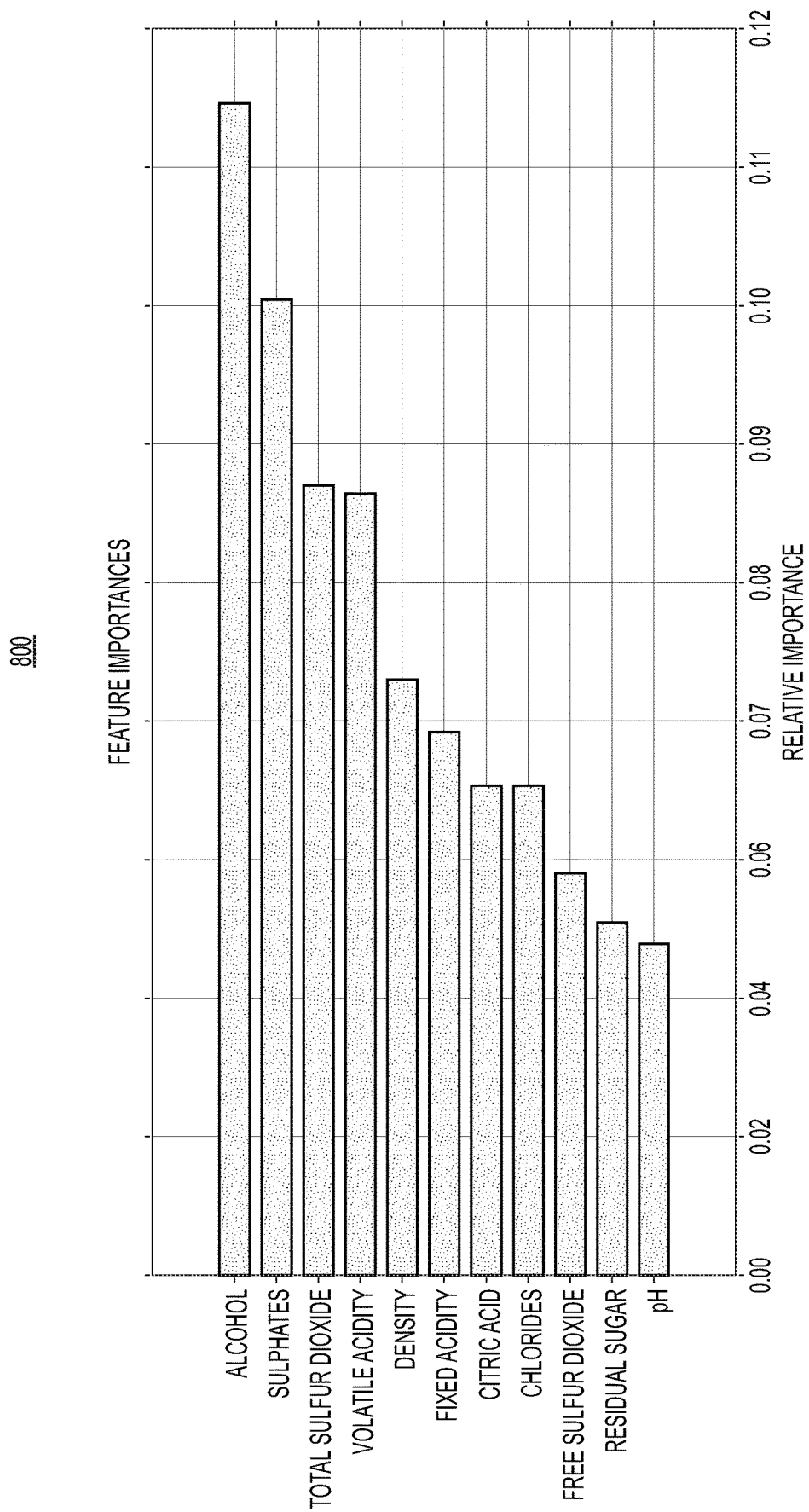
FIG. 8 shows a bar graph including the feature importance scores of the various features obtained in accordance with the examples disclosed herein.

FIG. 8 shows a bar graph 800 representing the feature importance scores of the various features in the sample historic experiments data set 750 that were obtained in accordance with the examples disclosed herein. The bar graph 800 plots the various features versus the relative importance. As seen from the bar graph 800, the amount of alcohol has the highest importance in the process of making wine followed by the amount of sulfates, and other attributes like density, fixed acidity, etc. It may be noted that the features for which the feature importance scores are obtained are extracted from the column names in the sample historic experiments data set 750. The feature importance scores are calculated using supervised ML models such as random forests, neural networks, etc., depending on the historic experiments data set.

Figure 9:
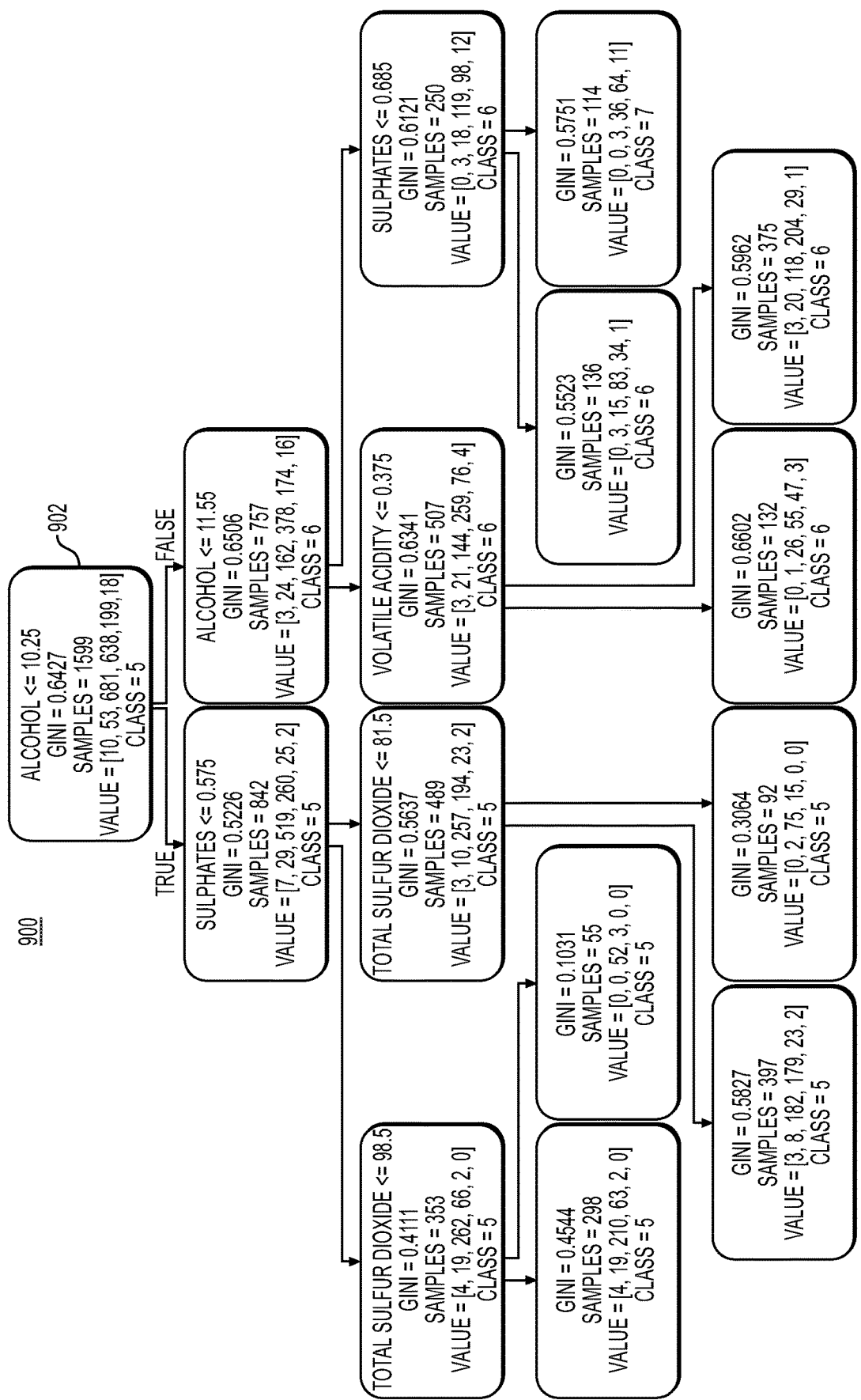
FIG. 9 shows a decision tree that was built from the historic experiments data set in accordance with the examples disclosed herein.

FIG. 9 shows a decision tree 900 that was built from the sample historic experiment data set 750 in accordance with the examples disclosed herein. The root node 902 pertains to alcohol which is the feature with the highest importance score and the lowest Gini index. Child nodes pertaining to features such as sulfates, total sulphur dioxide, volatile acidity, etc. are included in the decision tree 900. It may be noted that each of the features is associated with mathematical operators such as <=, >=, etc. and a corresponding numerical value which is indicative of a quantitative range for that ingredient/attribute.

FIG. 10 shows a table 1000 of analytical rules for synthesizing red wine that are generated in accordance with the examples disclosed herein. Particularly, the analytical rules shown in the table 1000 pertain to preparing red wine as detailed in the sample historical experiments data set 750. Each of the rules include a rule no., the chemical product 1002 to be synthesized, the target state 1004, the ingredients 1006, the units 1008 associated with the quantities of the ingredients, and the mathematical operators along with the corresponding numerical values 1010. The quantities of the ingredients therefore are expressed in terms of range thresholds that include the maximum and the minimum quantities of the ingredients that were included in the sample historical experiments data set 750. Each row of the table 1000 indicates one analytical rule that corresponds to one ingredient or product attribute and the thresholds associated with the amounts of ingredients that may be used for synthesizing the chemical product 1002. Based on the Max operator and the Min operator, the corresponding min and max quantities represent the upper and lower thresholds of the ingredient quantities that may be used for making the red wine.

FIG. 11 shows a formulation GUI 1100 that enables further customization and validation of the seed formulae by enabling users to generate intermediate formulae from seed formulae in accordance with the examples disclosed herein. The seed formulae developed from the analytical rules shown in table 1000 are displayed on the formulation GUI 1100. Different seed formulae 1110, 1120 and 1130 are directed towards a generating red wine of quality '5' at 1102 where the quality pertains to the target variable. The jurisdiction 1104 for which the formulation is being developed is shown along with the number 1106 of seed formulae including the total number of intermediate formulae. Each seed formula includes the ingredients and the amount of the ingredients to be used in the formulation as selected by the user from allowable ranges encoded in the rules shown in the table 1000. In an example, the formulation GUI 1100 may be configured so that user selections including the quantities of the ingredients stay within thresholds allowable by the analytical rules 116 so that no non-compliant intermediate formulae are even entered by the user. For example, the first seed formula 1110 for red wine is given as "alcohol+sulfates+total sulfur dioxide", with 10% alcohol, 0.575 g/ltr of sulfates and 81.5 mg/ltr. of total sulfur dioxide. Similarly, other seed formulations 1120 and 1130 with different amounts of the ingredients are also shown. The intermediate formulae are transmitted to a supervisory user who may approve or reject them. The approved intermediate formulae are stored as the final formulae 156 to be tested in the chemical lab 160.

Figure 12:
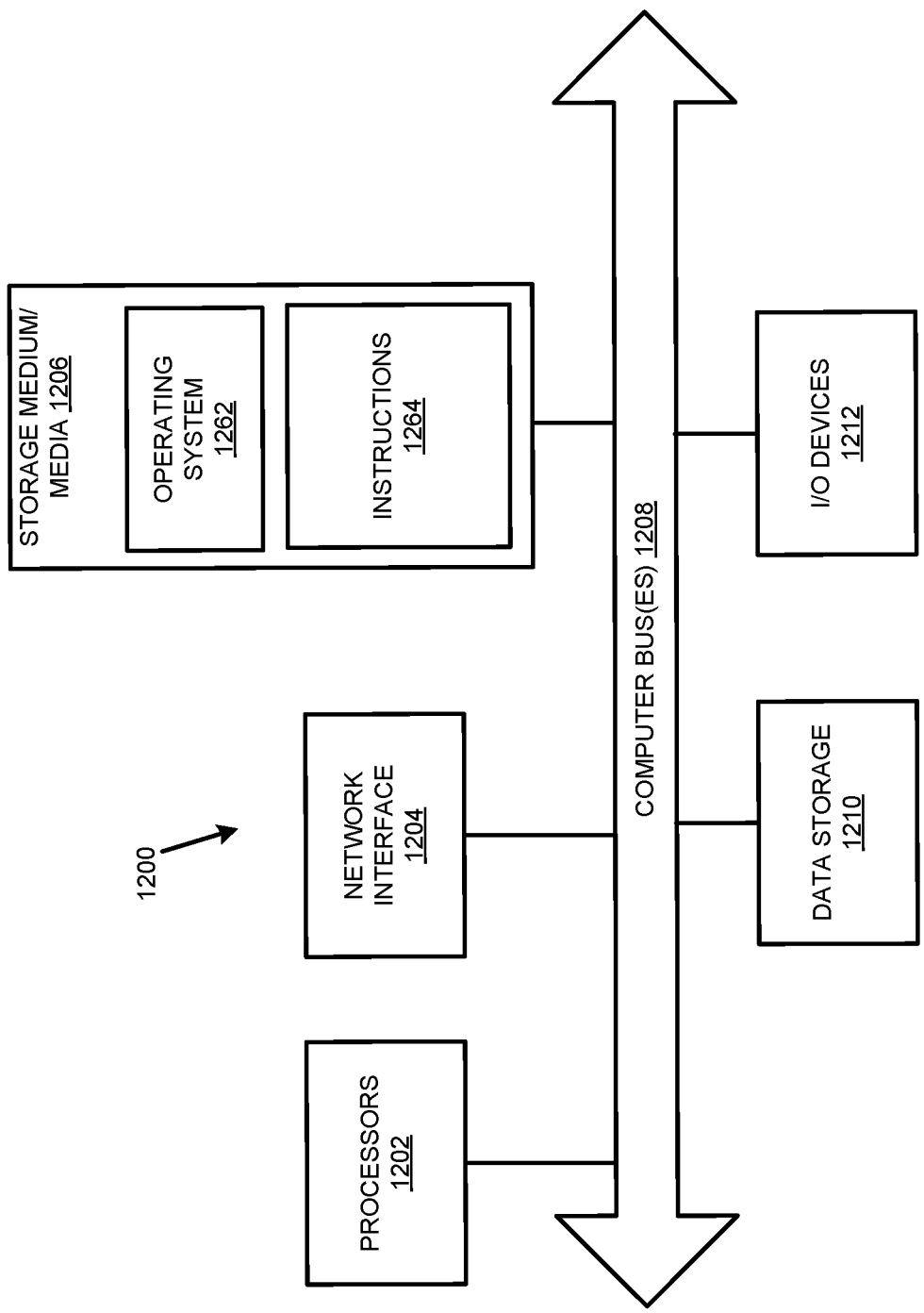
FIG. 12 illustrates a computer system that may be used to implement the chemical product formulation system in accordance with the examples disclosed herein.

FIG. 12 illustrates a computer system 1200 that may be used to implement the chemical product formulation system 100. More particularly, computing machines such as desktops, laptops, smartphones, tablets and wearables which may be used to generate or access the data from the chemical product formulation system 100 may have the structure of the computer system 1200. The computer system 1200 may include additional components not shown and that some of the process components described may be removed and/or modified. In another example, a computer system 1200 can sit on external-cloud platforms such as Amazon Web Services, AZURE® cloud or internal corporate cloud computing clusters, or organizational computing resources, etc.

The computer system 1200 includes processor(s) 1202, such as a central processing unit, ASIC or other type of processing circuit, input/output devices 1212, such as a display, mouse keyboard, etc., a network interface 1204, such as a Local Area Network (LAN), a wireless 802.11x LAN, a 3G or 4G mobile WAN or a WiMax WAN, and a computer-readable medium or processor-readable storage 1206. Each of these components may be operatively coupled to a bus 1208. The processor-readable storage 1206 may be any suitable medium that participates in providing instructions to the processor(s) 1202 for execution. For example, the processor-readable medium 1206 may be non-transitory or non-volatile medium, such as a magnetic disk or solid-state non-volatile memory or volatile medium such as RAM. The instructions or modules stored on the processor-readable medium 1206 may include machine-readable instructions 1264 executed by the processor(s) 1202 that cause the processor(s) 1202 to perform the methods and functions of the chemical product formulation system 100.

The chemical product formulation system 100 may be implemented as software stored on a non-transitory processor-readable medium and executed by the one or more processors 1202. For example, the processor-readable medium 1206 may store an operating system 1262, such as MAC OS, MS WINDOWS, UNIX, or LINUX, and code 1264 for the chemical product formulation system 100. The operating system 1262 may be multi-user, multiprocessing, multitasking, multithreading, real-time and the like. For example, during runtime, the operating system 1262 is running and the code for the chemical product formulation system 100 is executed by the processor(s) 1202.

The computer system 1200 may include a data storage 1210, which may include non-volatile data storage. The data storage 1210 stores any data used by the chemical product formulation system 100. The data storage 1210 may be used to store the data structures 114, the analytical rules 116, the seed formulae 154, intermediate formulae and the final formulae 156 and other data that is used by the chemical product formulation system 100.

The network interface 1204 connects the computer system 1200 to internal systems for example, via a LAN. Also, the network interface 1204 may connect the computer system 1200 to the Internet. For example, the computer system 1200 may connect to web browsers and other external applications and systems via the network interface 1204.

What has been described and illustrated herein is an example along with some of its variations. The terms, descriptions, and figures used herein are set forth by way of illustration only and are not meant as limitations. Many variations are possible within the spirit and scope of the subject matter, which is intended to be defined by the following claims and their equivalents.

What is claimed is:

1. A chemical product formulation system comprising:
   at least one processor;

a non-transitory, processor-readable medium storing machine-readable instructions that cause the at least one processor to:

access historical experiments data from a data store, wherein the historical experiments data includes data regarding experiments for synthesis of a chemical product, the historical experiments data including ingredients used for making the chemical product, proportions of the ingredients required to make the chemical product and specifications associated with each of the experiments;

identify features from the historical experiments data, wherein the features include at least attributes of the chemical product to be synthesized;

train a product-specific machine learning (ML) model on the historical experiments data to generate feature importance scores for the features,
wherein the product-specific ML model is trained via supervised learning on the historical experiments data of the chemical product to be synthesized;

obtain a feature importance score of each of the features from predictions of the product-specific machine learning (ML) model;

select a subset of the features including independent and dependent features based on the feature importance scores;

build data structures including at least a classification tree that encodes data pertaining to the subset of the features, wherein the classification tree includes a root node and child nodes,
wherein the subset of features are assigned to the root nodes and child nodes based on a cost function that evaluates splits in feature selection;

extract node attributes of the root node and the child nodes, wherein the node attributes include at least corresponding quantitative ranges associated with the subset of features, and the node attributes are extracted by applying at least natural language processing (NLP) and expression matching;

group the node attributes based on a target state, wherein the target state includes one of a process or a product criteria to be achieved during the synthesis of the chemical product;

generate a rules database on the non-transitory, processor-readable medium, the rules database is generated automatically from the data structures and the rules database stores the node attributes grouped by the target state as rules for synthesizing the chemical product, wherein the rules database includes at least columns for a rule number, the target state, ingredients for producing the chemical product, units for quantities of the ingredients and mathematical operators setting permissible ranges for the quantities, wherein the mathematical operators are included per the quantitative ranges in the node attributes;

generate seed formulae for the synthesis of the chemical product from the rules, wherein the seed formulae include at least ingredients and quantities of the ingredients to be used for the synthesis of the chemical product;

cause a display of the seed formulae on a formulation graphical user interface (GUI),
wherein the display of the seed formulae is enabled for user selections of the quantities of the ingredients within the permissible ranges set by the mathematical operators, and the permissible ranges are further restrained to values compliant with the regulations of a selected jurisdiction associated with production of the chemical product;

receive, via the formulation GUI, user selections for specific quantities for one or more of the ingredients;

store within the non-transitory, processor-readable medium as intermediate formulae, the seed formula including the specific quantities of the one or more ingredients; and provide one or more of the intermediate formulae that are validated and stored as final formulae to a production system for making the chemical product.

2. The chemical product formulation system of claim 1, wherein the processor is to further:
preprocess the historical experiments data by improving data density and via data deduplication.

3. The chemical product formulation system of claim 1, wherein the processor is to further:
identify target features and explanatory features from the features extracted from the historical experiments data.

4. The chemical product formulation system of claim 1, wherein the product-specific ML model includes decision trees, and to select the subset of the features the processor is to further:
obtain the feature importance scores by calculating Gini index for each node in each decision tree.

5. The chemical product formulation system of claim 4, wherein to select the subset of the features, the processor is to further:
normalize the feature importance values.

6. The chemical product formulation system of claim 4, wherein to calculate the Gini index the processor is to further:
build the product-specific ML model including a classification and regression tree (CART).

7. The chemical product formulation system of claim 6, wherein to build the CART the processor is to further:
evaluate split in feature selection using the Gini index as the cost function for the generation of the CART.

8. The chemical product formulation system of claim 1, wherein to extract the rules for synthesizing the chemical product the processor is to:
identify the root node and the child nodes of a classification and regression tree (CART) encoding the subset of features.

9. The chemical product formulation system of claim 1, wherein to extract the rules for synthesizing the chemical product the processor is to:
store the node attributes as entries into a textual data file.

10. The chemical product formulation system of claim 1, wherein to generate the seed formulae for the synthesis of the chemical product the processor is to:
identify from the rules, the ingredients and range thresholds for the quantities of the ingredients to be used for synthesizing the chemical product in accordance with a quality criterion.

11. The chemical product formulation system of claim 1, wherein to provide the seed formulae that are validated to the production system the processor is to:
provide the intermediate formulae to a supervisory user for validation; and
receive validated intermediate formulae as the final formulae.

12. The chemical product formulation system of claim 1, wherein to provide the seed formulae that are validated to the production system the processor is to:

transmit at least one of the final formulae to the production system for the synthesis of the chemical product.

13. The chemical product formulation system of claim 12, wherein the processor is to further:
receive post-production data of the final formulae used for the synthesis of the chemical product from the production system; and
add the post-production data of the final formulae to the historic experiments data.

14. A method of synthesizing a chemical product comprising:
preprocessing, by at least one processor, historic experiments data retrieved from a data store, wherein the historic experiments data that includes ingredients used for synthesizing the chemical product in prior experiments, quantities of the ingredients used for the synthesis of the chemical product in the historic experiments, specifications of the chemical product that was synthesized and outcomes of the historic experiments;
receiving, by the at least one processor, information regarding independent features and dependent features from the historic experiments data, wherein the features include at least attributes of the chemical product to be synthesized;
training, by the at least one processor, a product-specific machine learning (ML) model on the historical experiments data to generate feature importance scores for the features,
wherein the product-specific ML model is trained via supervised learning on the historical experiments data of the chemical product to be synthesized;
obtaining, by the at least one processor, feature importance scores of the independent features and the dependent features from predictions of the trained product-specific machine learning (ML) model;
constructing, by the at least one processor, data structures including a classification tree with a root node and child nodes encoding the historic experiments data of a subset of the features that are selected based on the feature importance scores and the subset of features are assigned to the root nodes and child nodes based on a cost function that evaluates splits in feature selection;
extracting, by the at least one processor, node attributes of the root node and the child nodes, wherein the node attributes include at least corresponding quantitative ranges associated with the subset of features, and the node attributes are extracted by applying at least natural language processing (NLP) and expression matching;
grouping, by the at least one processor, the node attributes based on a target state, wherein the target state includes one of a process or a product criteria to be achieved during the synthesis of the chemical product;
generating, by the at least one processor, a rules database that stores the node attributes grouped by the target state as analytical rules for synthesizing the chemical product, wherein the rules database is generated automatically from the data structures and the rules database includes at least columns for a rule number, the target state, the ingredients and the quantities of ingredients to be used expressed in terms of mathematical operators that set thresholds including minimum and maximum quantities of the ingredients, wherein the mathematical operators are included per the quantitative ranges in the node attributes;
generating, by the at least one processor, seed formulae from the analytical rules, the seed formulae including the ingredients and the quantities of ingredients to be used for the synthesis of the chemical product;
causing, by the at least one processor, a display of the seed formulae on a formulation graphical user interface (GUI), wherein the display of the seed formulae is enabled for user selections of the quantities of the ingredients within the minimum and maximum quantities of the ingredients set by the mathematical operators, and
the minimum and maximum quantities of the ingredients are further restrained to values compliant with the regulations of a selected jurisdiction associated with production of the chemical product;
enabling, by the at least one processor, a user to generate one or more intermediate formulae from the seed formulae via displaying the seed formula on a formulation graphical user interface (GUI) that enables the user to select specific quantities for each of the ingredients;
receiving, by the at least one processor via the formulation GUI, user inputs adjusting the quantities of one or more of the ingredients;
storing, by the at least one processor, as intermediate formulae within a non-transitory, processor-readable medium coupled to the formulation GUI, the seed formula including the adjustments of the quantities of the one or more ingredients; and
providing, by the at least one processor, one or more of validated ones of the intermediate formulae as final formulae to a production system.

15. The method of claim 14, wherein the trained product-specific ML model includes a random forest model or a neural network.

16. The method of claim 14, wherein each of the seed formulae includes the ingredients and an allowable range of quantities of the ingredients to be added.

17. A non-transitory, processor-readable storage medium comprising machine-readable instructions that cause a processor to:
access historical experiments data that includes data regarding experiments for synthesis of a chemical product, the historical experiments data including ingredients used for making the chemical product, proportions of the ingredients required to make the chemical product and specifications associated with each of the experiments;
extract features from the historical experiments data using a feature selection algorithm, wherein the features include at least attributes of the chemical product to be synthesized;
train a product-specific machine learning (ML) model on the historical experiments data to generate feature importance scores for the features,
wherein the product-specific ML model is trained via supervised learning on the historical experiments data of the chemical product to be synthesized;
obtain a feature importance score of each of the features from predictions of the product-specific machine learning (ML) model;
select a subset of the features including independent and dependent features based on the feature importance scores;
build data structures including at least a classification tree that encodes data pertaining to the subset of the features, wherein the classification tree includes a root node and child nodes, wherein the root nodes and child nodes are selected based on a cost function that evaluates splits in feature selection;

extract node attributes of the root node and the child nodes, wherein the node attributes include at least corresponding quantitative ranges associated with the subset of features, and the node attributes are extracted by applying at least natural language processing (NLP) and expression matching;

group the node attributes based on a target state, wherein the target state includes one of a process or a product criteria to be achieved during the synthesis of the chemical product;

generate a rules database that stores the node attributes grouped by the target state as rules for synthesizing the chemical product, wherein the rules database is generated automatically from the data structures and the rules database includes at least columns for a rule number, the target state, ingredients for producing the chemical product, units for quantities of the ingredients and mathematical operators setting permissible ranges for the quantities, wherein the mathematical operators are included per the quantitative ranges in the node attributes;

generate seed formulae for the synthesis of the chemical product from the rules, wherein the seed formulae include at least ingredients and quantities of the ingredients to be used for the synthesis of the chemical product;

cause a display of the seed formulae on a formulation graphical user interface (GUI) wherein the display of the seed formulae is enabled for user selections of the quantities of the ingredients within the permissible ranges set by the mathematical operators, and the permissible ranges are further restrained to values compliant with the regulations of a selected jurisdiction associated with production of the chemical product;

receive, via the formulation GUI, user inputs adjusting the quantities of one or more of the ingredients;

store within the non-transitory, processor-readable medium as intermediate formulae, the seed formula including the adjustments of the quantities of the one or more ingredients; and provide one or more of the intermediate formulae that are validated to a production system for production of the chemical product.

* * * * *